United States Patent
Peerce et al.

(10) Patent No.: US 8,921,343 B2
(45) Date of Patent: Dec. 30, 2014

(54) ARYLFLUOROPHOSPHATE INHIBITORS OF INTESTINAL APICAL MEMBRANE SODIUM/PHOSPHATE CO-TRANSPORT

(75) Inventors: Brian Peerce, Friendswood, TX (US); Larry Slomowitz, Vancouver (CA)

(73) Assignee: Duophos, Friendswood, TX (US)

( * ) Notice: Subject to any disclaimer, the term of this patent is extended or adjusted under 35 U.S.C. 154(b) by 73 days.

(21) Appl. No.: 13/582,728

(22) PCT Filed: Mar. 4, 2011

(86) PCT No.: PCT/US2011/027232
§ 371 (c)(1),
(2), (4) Date: Nov. 15, 2012

(87) PCT Pub. No.: WO2011/109731
PCT Pub. Date: Sep. 9, 2011

(65) Prior Publication Data
US 2013/0059822 A1 Mar. 7, 2013

Related U.S. Application Data

(60) Provisional application No. 61/310,902, filed on Mar. 5, 2010.

(51) Int. Cl.
*A61K 31/66* (2006.01)
*C07F 9/02* (2006.01)
*C07F 9/14* (2006.01)

(52) U.S. Cl.
CPC .................................. *C07F 9/1406* (2013.01)
USPC .............................. 514/125; 558/89; 558/195

(58) Field of Classification Search
CPC .................................. C07F 9/14; C07F 9/1406
USPC .............................. 514/125; 558/70, 89, 195
See application file for complete search history.

(56) References Cited

PUBLICATIONS

Peerce et al., "A phosphorylated phloretin derivative. Synthesis and effect on intestinal Na+ -dependent phosphate absorption", Oct. 2002; Am J Physiol Gastrointest Liver Physiol, vol. 283, pp. G848-G855.*
Dabkowski et al., "Synthesis of phosphorofluoridates and phosphorofluoridothioates via the phosphoramidite approach", 2005, Or. Biomol. Chem., vol. 3, pp. 866-874.*
Romanenko et al., "Fluorinated organophosphates for biomedical targets", 2008, Tetrahedron, vol. 64, pp. 6153-6190.*

* cited by examiner

*Primary Examiner* — My-Chau T Tran
(74) *Attorney, Agent, or Firm* — Occhiuti & Rohlicek LLP

(57) ABSTRACT

The present invention is directed to fluorophosphates, and pharmaceutical compositions thereof, which are inhibitors of intestinal apical sodium/phosphate co-transport and are useful in the treatment of hyperphosphatemia, in reducing blood phosphate levels, and in treating hypertension.

20 Claims, No Drawings

ARYLFLUOROPHOSPHATE INHIBITORS OF INTESTINAL APICAL MEMBRANE SODIUM/PHOSPHATE CO-TRANSPORT

CROSS REFERENCE TO RELATED APPLICATIONS

This application is a U.S. national phase application filed under 35 U.S.C. §371 of International Application No. PCT/US2011/027232, which was filed Mar. 4, 2011, and which claims the benefit of the filing date of U.S. Provisional Application No. 61/310,902, which was filed Mar. 5, 2010.

FIELD OF THE INVENTION

This invention relates to hydrophilic aryl fluorophosphates that act to inhibit intestinal apical membrane Na-mediated phosphate co-transport, effective treatments to reduce blood phosphate, methods of treating hyperphosphatemia, and methods of making inhibitors.

BACKGROUND OF THE INVENTION

Secondary hyperparathyroidism is a common and severe complication of chronic renal failure (CRF) resulting in renal osteodystrophy, hypertension, metabolic acidosis, and contributing to cardiac disease. Hyperphosphatemia due to decreased renal phosphate excretion is thought to contribute to secondary hyperparathyroidism in patients with chronic renal insufficiency. Recently, it has been established that decreasing the phosphate load can reduce secondary hyperparathyroidism and possibly preserve renal function.

In mammals, intestinal phosphate absorption occurs at the brush border membrane in the proximal intestine (duodenum and jejunum). Phosphate absorption has an active component and a passive component. Active uptake of phosphate is coupled to $Na^+$ uptake down its electrochemical potential gradient by the $Na^+$/phosphate cotransporter. The active component of phosphate absorption is regulated by dietary phosphorus and serum 1,25 dihydroxyvitamin $D_3$. Changes in dietary phosphorus have been reported to alter expression of NaPi II b in the intestine. $Na^+$-independent phosphate uptake occurs by an unknown mechanism down its electrochemical potential gradient. The mechanism of phosphate transport across the intestinal basolateral membrane has not been defined Chalcones are a class of aromatic ketones with important biological activity and their effect on membrane transport is well known. Phloridzin, a member of the chalcones, is a potent inhibitor of the renal and intestinal brush border membrane $Na^+$/glucose cotransporters. The aglucone of phloridzin, phloretin, inhibits a variety of membrane transporters including Band 3 (AE-1, 9, 10) and the facilitated diffusion glucose carrier (GLUT-4, 9, 14). A phosphorylated phloretin derivative, 2'-PP, has been shown to be a potent inhibitor of the intestinal $Na^+$/phosphate cotransporter but not the primary renal proximal tubule $Na^+$/phosphate cotransporter. The major limitation of 2'-PP for the treatment of hyperphosphatemia is that it is a phosphate ester, and therefore, it is degraded by phosphatases, including the intestinal apical membrane phosphatase, alkaline phosphatase.

Thus, new or improved agents which inhibit intestinal apical membrane $Na^+$-mediated phosphate co-transport are continually needed for developing new and more effective pharmaceuticals that are aimed at the treatment of secondary hyperparathyroidism caused by CRF and resulting in renal osteodystrophy, hypertension, metabolic acidosis, and contributing to cardiac disease. 2'-FPP which is 30 times more potent than 2'-PP and is also more stable to esterases represents a major advance and improvement over 2'-PP well known to be efficacious in the treatment of CRF. The compounds, compositions and methods described herein are directed toward these needs and other ends.

SUMMARY OF THE INVENTION

The present invention provides, inter alia, compounds conforming to Formula I:

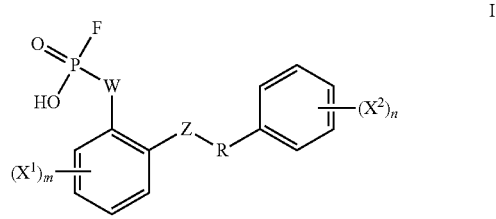

or a pharmaceutically acceptable salt thereof, wherein constituent members are defined herein. The compounds can inhibit intestinal apical membrane sodium-mediated phosphate co-transport.

The present invention further provides pharmaceutical compositions comprising a compound of Formula I, or a pharmaceutically acceptable salt thereof, and at least one pharmaceutically acceptable carrier. The compound can be present in an amount that confers a clinically beneficial result on a patient to whom the compound has been administered. Thus, the compositions can include therapeutically effective amounts of the compounds described herein.

The present invention further provides methods of inhibiting intestinal apical sodium/phosphate cotransport, comprising contacting the intestinal epithelium with a compound of Formula I, or a pharmaceutically acceptable salt thereof.

The present invention further provides methods of treating a disease or a disorder associated with abnormal blood phosphate levels in a patient by administering to a patient a therapeutically effective amount of a compound of Formula I, or a pharmaceutically acceptable salt of the same.

The present invention further provides methods of treating diseases such as chronic renal failure, renal osteodystrophy, hypertension, metabolic acidosis, and cardiac disease in a patient by administering to the patient a compound of Formula I, or a pharmaceutically acceptable salt thereof. The renal failure can be end-stage renal failure.

The present invention further provides a compound of Formula I, or a pharmaceutically acceptable salt thereof, for use in the preparation of a medicament or for the production of a medicament for use in therapy, including therapy for a condition described herein.

The present invention provides processes for preparing a compound of Formula I:

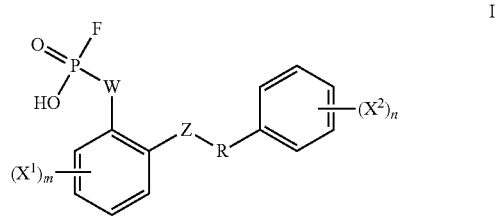

or a pharmaceutically acceptable salt thereof, wherein R is $C_{2-4}$ alkyl; W is selected from $NR^4$, O, and S; Z is selected from a single bond, —C(O)—, $NR^4$, O, and S; $X^1$ and $X^2$ are each independently selected from —OH, —NHR$^A$, and —C(O)OH; R$^A$ is H or C$_{1-3}$ alkyl; m is 1, 2, 3, or 4; and n is 1, 2, 3, or 4.

The present invention provides processes for preparing a compound of Formula I-1:

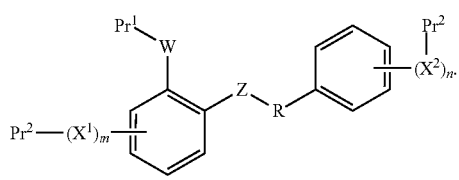

I-1

The present invention provides processes for preparing a compound of Formula I-2:

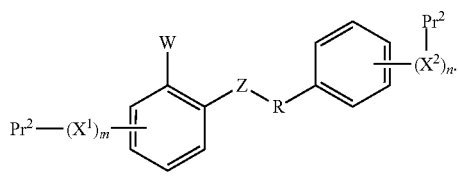

I-2

The present invention provides processes for preparing a compound of Formula I-3:

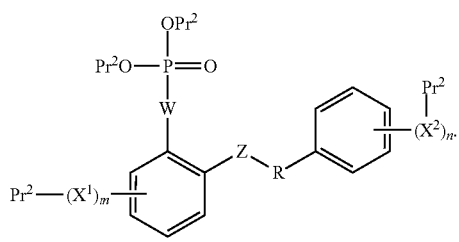

I-3

The present invention provides processes for preparing a compound of Formula I-4:

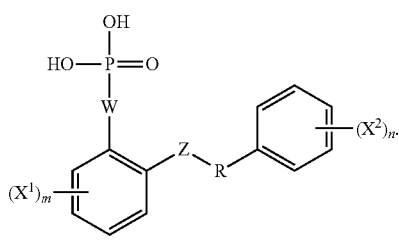

I-4

DETAILED DESCRIPTION

The present invention provides, inter alia, compounds that inhibit apical Na/phosphate cotransport and are useful, for example, to reduce blood phosphate levels, and in the treatment of hyperphosphatemia. The compounds of the invention include those having Formula I:

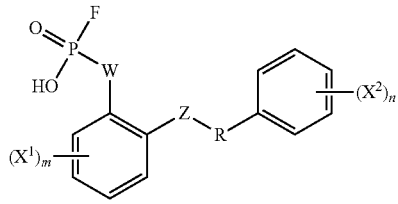

I or a pharmaceutically acceptable salt thereof, wherein:
R is C$_{2-4}$ alkyl;
W is selected from NR$^A$, O, and S;
Z is selected from a single bond, —C(O)—, NR$^A$, O, and S;
X$^1$ and X$^2$ are each independently selected from —OH, —NHR$^A$, and —C(O)OH;
R$^A$ is H or C$_{1-3}$ alkyl;
m is 1, 2, 3, or 4; and
n is 1, 2, 3, or 4.

In other embodiments, X$^1$ and X$^2$ are each independently selected from OR$^1$ and OR$^2$, wherein R$^1$ and R$^2$ are independently H or a protecting group. In other embodiments, X$^1$ and X$^2$ are independently selected from COOR$^1$ and COOR$^2$, wherein R$^1$ and R$^2$ are independently H or a protecting group.

In some embodiments, R is —CH$_2$—CH$_2$— or —CH$_2$—CH$_2$—CH$_2$—.

In some embodiments, W is selected from NR$^A$ and O.

In some embodiments, W is O.

In some embodiments, Z is selected from a single bond and —C(O)—.

In some embodiments, Z is —C(O)—.

In some embodiments, X$^1$ and X$^2$ are independently selected from OH and NH$_2$.

In some embodiments, X$^1$ and X$^2$ are both OH.

In some embodiments, n is 1 or 2.

In some embodiments, m is 1 or 2.

In some embodiments, m is 2 and n is 1.

In some embodiments, R is —CH$_2$—CH$_2$— and Z is —C(O)—.

In some embodiments, W is O, and X$^1$ and X$^2$ are both OH.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, sec-butyl, t-butyl), pentyl (e.g., n-pentyl, isopentyl, sec-pentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. Examples of bicyclic heteroaryl groups include without limitation, purinyl, indolyl, and the like. In some embodiments, any ring-forming N in a heteroaryl moiety can be substituted by oxo. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 9 to about 10, or 5 to 6 ring-forming atoms. In some embodiments, the heteroaryl group has 1 to about 4, 1 to about 3, or 1 to 2 heteroatoms.

It should be further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers, and isotopes of the structures depicted, including structures conforming to a generic formula set out herein.

All compounds, and pharmaceutically acceptable salts thereof, can be found together with other substances such as water and solvents (e.g. hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis:

The processes and intermediates of the present invention are useful in the preparation of inhibitors of intestinal apical sodium/phosphate cotransport, effective in reducing blood phosphate levels and hyperphosphatemia. Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Example synthetic methods for preparing compounds of the invention are provided in the Schemes below. For instance, compounds of the invention can be prepared by the general retrosynthetic scheme shown in Scheme 1. Compounds of formula 1 can be prepared by subjecting a compound of formula 2 with a fluorinating agent. Compounds of formula 2 can be synthesized by removing Pr$^2$ from a compound of formula 3. Compounds of formula 3 can be readily prepared from the phosphorylation of compounds of formula 4. Finally, compounds of formula 5 can be synthesized via the selective deprotection revealing the attachment point (W) for phosphorylation.

Scheme 1

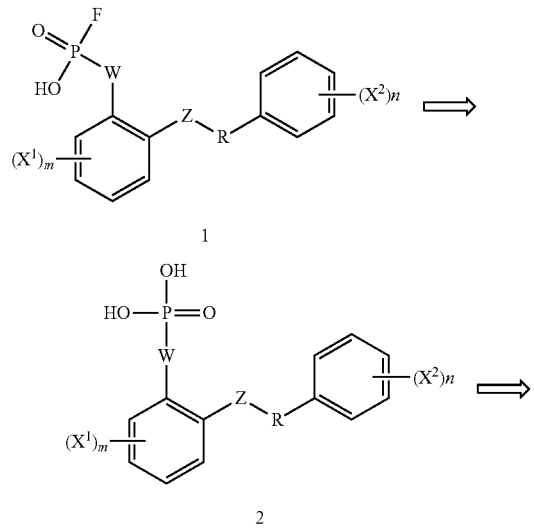

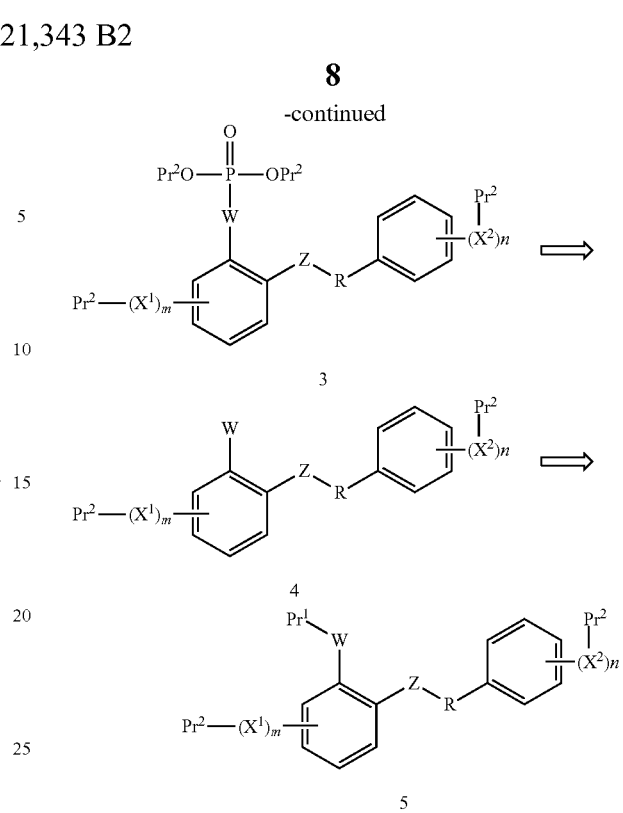

Accordingly, the present invention provides a process for preparing a compound of Formula I:

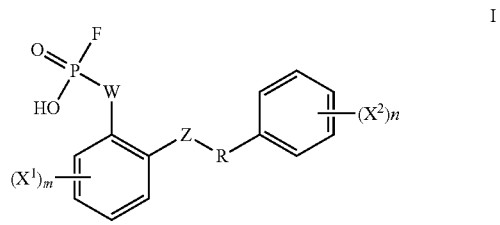

or a pharmaceutically acceptable salt thereof, wherein R is $C_{2-4}$ alkyl;

W is selected from $NR^4$, O, and S; Z is selected from a single bond, —C(O)—, $NR^4$, O, and S; $X^1$ and $X^2$ are each independently selected from —OH, —$NHR^4$, and —C(O)OH; $R^4$ is H or $C_{1-3}$ alkyl; m is 1, 2, 3, or 4; and n is 1, 2, 3, or 4;

the process comprising:

a) removing Pr$^1$ in the presence of Pr$^2$ from a compound of Formula I-1:

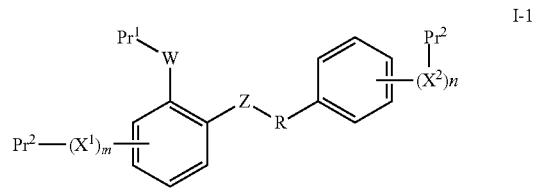

wherein Pr$^1$ and Pr$^2$ are protecting groups; to prepare a compound of Formula I-2:

fluorinating agent such as dinitrofluorobenzene (DNFB) or hydrofluoric acid (HF) to provide 2'-fluorophosphophloretin (10).

b) reacting a compound of Formula I-2 with a phosphorylating agent to prepare a compound of Formula I-3:

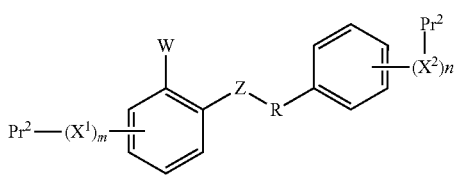

c) removing $Pr^2$ from a compound of Formula I-3 with a reducing agent to prepare a compound of Formula I-4:

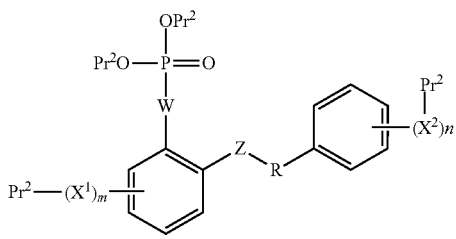

d) reacting a compound of Formula I-4 with a fluorinating agent to prepare said compound of Formula I.

In some embodiments, $Pr^1$ is:

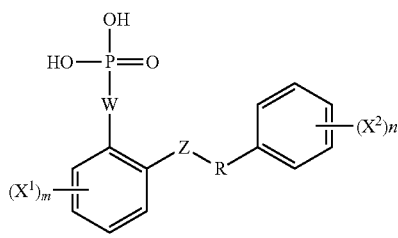

In some embodiments, $Pr^2$ is benzyl.

In some embodiments, the phosphorylating agent is a phosphite ester. In a further embodiment, the phosphite ester is dibenzyl phosphite. In another embodiment, the phosphorylating agent is a phosphonic acid. In a further embodiment, the phosphonic acid is fluorophosphonic acid.

In some embodiments, the reducing agent is comprised of hydrogen gas and a transition metal.

In some embodiments, the fluorinating agent is dinitrofluorobenzene. In a further embodiment, the fluorinating agent is hydrofluoric acid.

As shown in Scheme 2, the known compound phloridzin is benzylated to provide the fully benzyl-protected compound 6. Treatment of compound 6 under acidic conditions provided phenol 7 which was converted into the benzyl-protected phosphate compound 8. Catalytic hydrogenation of 8 provided 2'-phosphophloretin (9) which was fluorinated with a Scheme 2

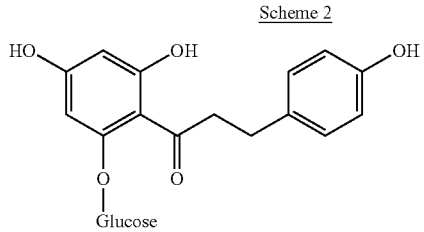
Phloridzin

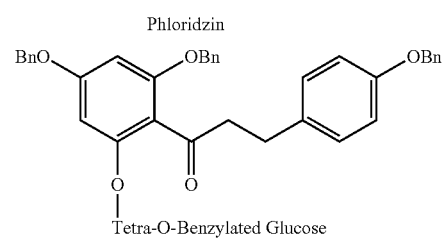

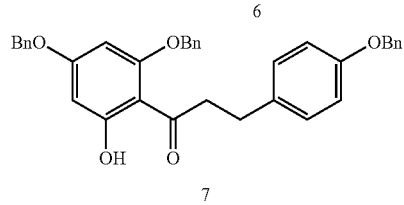
7

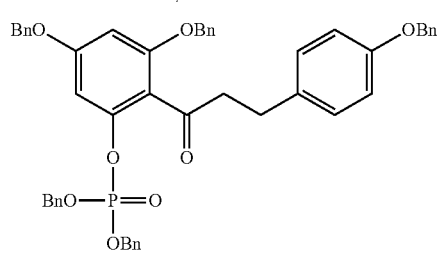
8

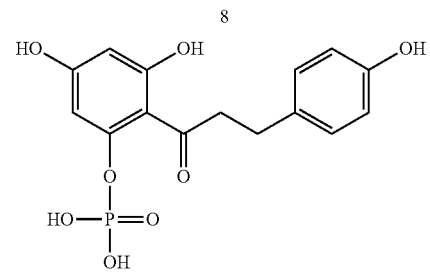
9
2'-Phosphophloretin

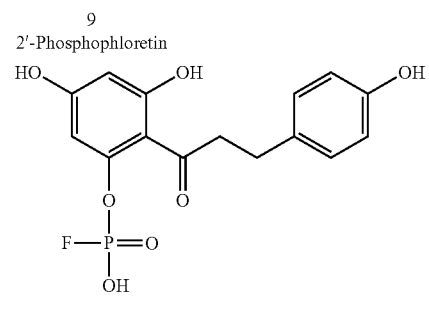
10
2'-flurophosphophloretin

Alternatively, 2' phosphophloretin (9) can be fluorinated using anhydrous hydrofluoric acid to yield 2'-fluorophosphophloretin (10) (Scheme 3).

Scheme 3

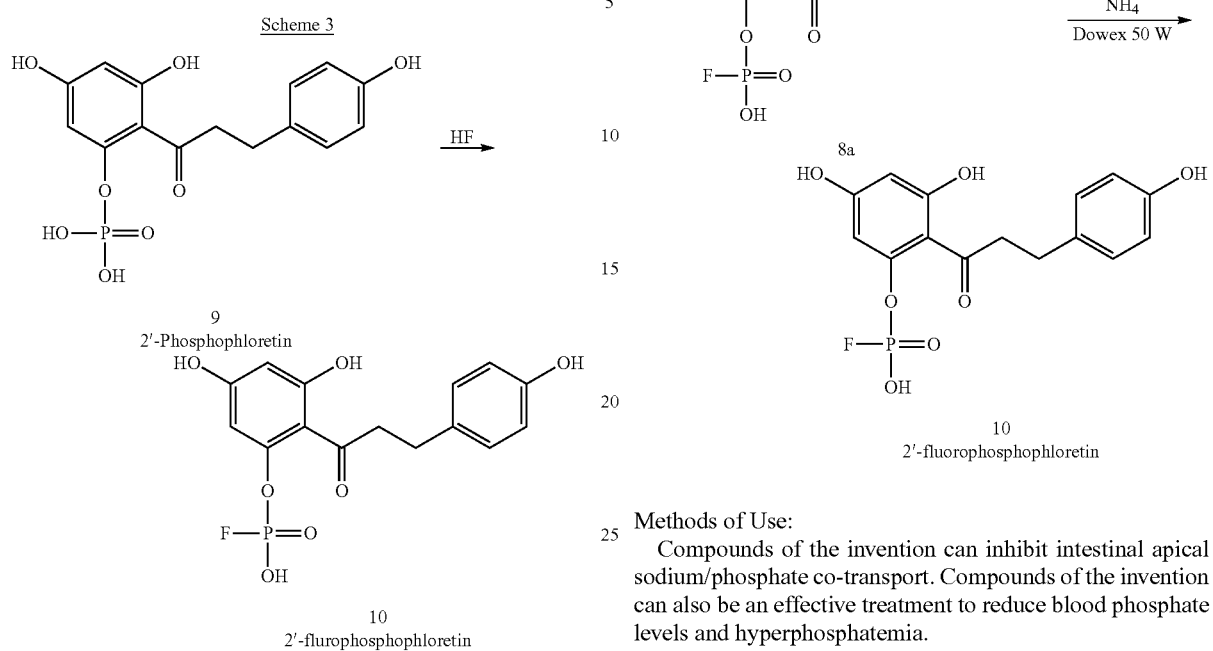

9
2'-Phosphophloretin 10
2'-flurophosphophloretin

An alternative route to preparing 2'-fluorophosphophloretin is shown in Scheme 4 starting from the known compound phloridzin. Benzylation of phloridzin provided 6 which was selectively deprotected to provide the phenol 7. Treatment with dichlorochromate (DCC) and fluorophosphonic acid afforded the fluorophosphonic acid 8a. Removal of the benzyl groups of 8a was accomplished using ammonium and Dowex 50W to provide 2'-fluorophosphophloretin.

Scheme 4

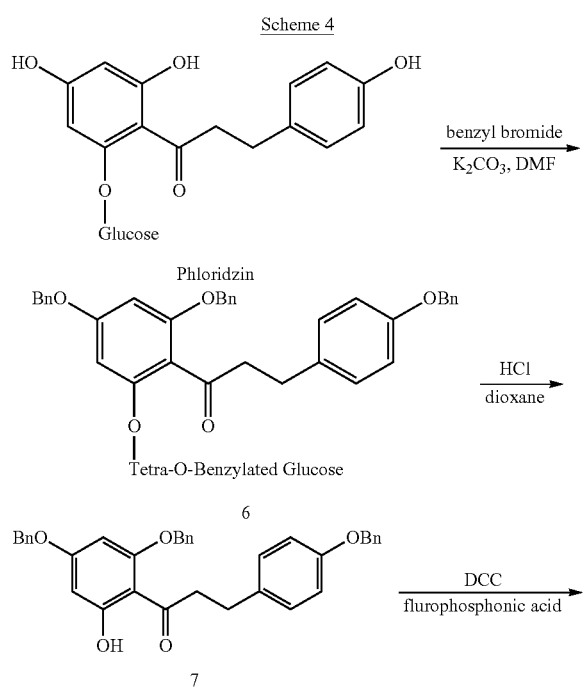

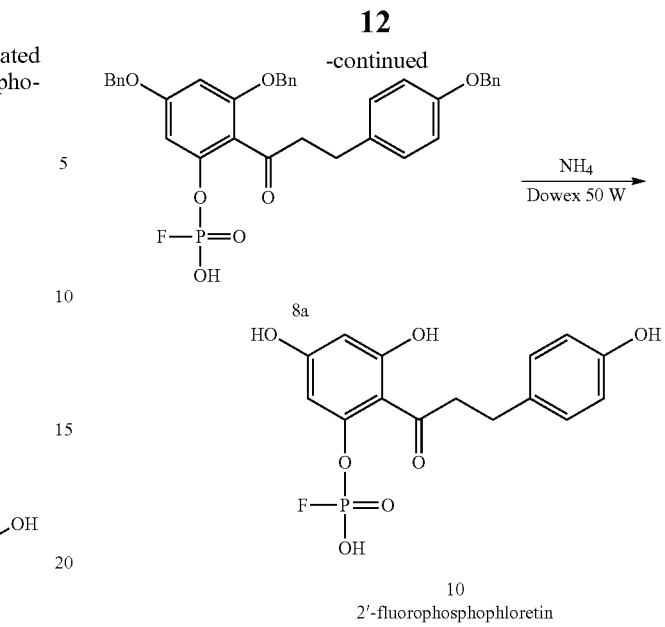

8a 10
2'-fluorophosphophloretin

Methods of Use:

Compounds of the invention can inhibit intestinal apical sodium/phosphate co-transport. Compounds of the invention can also be an effective treatment to reduce blood phosphate levels and hyperphosphatemia.

The present invention further provides methods for treating a disease caused by or associated with elevated blood phosphate levels in a mammalian subject, including identifying a subject in which reduction of blood phosphate levels is desirable, and administering to the subject in need of such treatment a therapeutically effective amount or dose of a compound of the present invention or a pharmaceutical composition thereof. In some embodiments, the subject is a mammal. In some embodiments, the subject is a human. In some embodiments, the compound is administered orally. In some embodiments, the disease is chronic renal failure. In some embodiments, chronic renal failure is associated with and/or accompanied by hyperphosphatemia, secondary hyperparathyroidism, renal osteodystrophy, hypertension, metabolic acidosis, or cardiac disease. The chronic renal failure may be end-stage renal failure, and patients suffering from end-stage renal failure are amenable to treatment as described herein.

As used herein, the term "contacting" refers to the bringing together of indicated moieties in an in vitro system or an in vivo system. For example, "contacting" a compound of the invention with the intestinal apical sodium/phosphate co-transport includes the administration of a compound of the present invention to an individual or patient, such as a human, as well as, for example, introducing a compound of the invention into a sample containing a cellular or purified preparation of the intestinal apical sodium/phosphate co-transport.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Pharmaceutical Formulations and Dosage Forms:

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be oral.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for oral administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, soft and hard gelatin capsules, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compounds or compositions of the invention contain from about 5 to about 50 mg of the active ingredient. One having ordinary skill in the art will appreciate that this embodies compounds or compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compounds or compositions of the invention contain from about 50 to about 500 mg of the active ingredient. One having ordinary skill in the art will appreciate that this embodies compounds or compositions containing about 50 to about 100, about 100 to about 150, about 150 to about 200, about 200 to about 250, about 250 to about 300, about 350 to about 400, or about 450 to about 500 mg of the active ingredient.

In some embodiments, the compounds or compositions of the invention contain from about 500 to about 1000 mg of the active ingredient. One having ordinary skill in the art will appreciate that this embodies compounds or compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

In some embodiments, the compositions are administered by the oral route for local effect. Solution, suspension, or powder compositions can be administered orally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day.

In studies with 2'-phosphophoiretin, we administered to animals 0.1 g/day and observed no side effects over a 3-month trial in normal or $5/6^{th}$ nephrectomy rats. In other studies, with 2'-phosphofluoro phloretin, we administered to animals 0.02 g/day. We observed no side effects over a 2-month trial in normal rats; over a 1-month trial in $5/6^{th}$ nephrectomy rats; and over a 1-month trial in Dahl-salt sensitive rats. Our compounds compared favorably with calcium salts (such as TUMS®), LaCO$_3$ (FOSRENOL®), and a phosphorous binding resin (RENAGEL®).

In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

EXAMPLES

Example 1

Synthesis of 2'-fluorophosphophloretin (2'-FPP) using Dinitrofluorobenzene (DNFB)

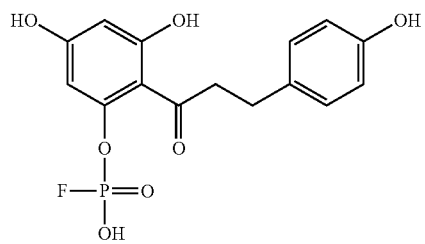 [SMILES: O=C(CCc1ccc(O)cc1)c1c(O)cc(O)cc1OP(=O)(O)F]

2'-fluorophosphphloretin (2'-FPP) was synthesized according to the method of Peerce et al. *Am. J. Physiol. Gastrointest. Liver Physiol.* 283: G848-G855, 2002.

Step 1. 4,6,4-tri-O-benzylphloretin

Phloridzin (2 g) was dissolved in redistilled dimethylformamide (35 ml) and potassium carbonate (3.1 g). Benzylbromide (2.7 ml) was added to this solution and the reaction mixture was allowed to stir for 3 days at 23° C. The solution was distilled under vacuum, and the residue was cooled to room temperature. The residue was extracted with water/ethyl acetate (2:1) three times. The organic layers were combined and concentrated in vacuo. The residue was dissolved in 1,4 dioxane (200 ml), and HCl was added dropwise to a final concentration of 0.4 N. The mixture was refluxed for 3 hours. The reaction mixture was cooled, diluted with 1 M sodium bicarbonate, and extracted with ethyl acetate. The ethyl acetate extraction was repeated three times. The combined organic extracts were washed with water, followed by two washes with NaCl (0.9%). Anhydrous Na$_2$SO$_4$ was added to the organic layer and mixed. Vacuum filtration removed the Na$_2$SO$_4$. Fresh Na$_2$SO$_4$ was added to the solution, which was then stirred for 12 hours at 23° C. Vacuum filtration removed the Na$_2$SO$_4$, and the filtrate was concentrated to yield 4,6,4-tri-O-benzylphloretin (2.1 g, 92% yield): $^1$H-NMR (CDCl$_3$) δ13.6 (s, 1H); 7.46-7.29 (m, 15H); 6.86 (d, J=8.8 Hz, 2H); 6.8 (d, J=8.8 Hz, 2H); 6.35 (d, J=2.3 Hz, 1H); 6.21 (d, J=2.3 Hz, 1H); 5.17 (s, 2H); 5.14 (s, 2H); 5.07 (s, 2H); 3.2 (t, J=7.1 Hz, 2H) ppm.

Step 2. Dibenzylphosphotribenzyl phloretin 4,6,4-Tri-O-benzylphloretin (2.1 g) was dissolved in N,N-dimethylacetamide (DMAc) and placed on ice. Sodium hydride (60%) was added, and the mixture was stirred at 23° C. for 1 hour. The solution was cooled, and the sodium hydride was inactivated with carbon tetrachloride. Dibenzylphosphite (1.31 ml) in N,N-dimethylacetamide was added, and the solution was stirred for 30 min. The solution was acidified and partitioned between water and hexane/ethyl acetate (1:1). The water layer was extracted three times with hexane/ethyl acetate. The combined organic layers were washed with 0.9% NaCl and dried over anhydrous sodium sulfate. Sodium sulfate was removed by filtration. The filtrate was concentrated in vacuo and purified by chromatography on silica gel using ethyl acetate/dichloromethane/hexanes (5:25:70) as the eluant. Dibenzylphosphotribenzyl phloretin (750 mg, 43% yield) was recovered: $^1$H-NMR (CDCl$_3$) δ 7.42-7.29 (m, 25H); 6.93 (d, J=8.8 Hz, 2H); 6.78 (d, J=8.8 Hz, 2H); 6.63 [double doublet (dd), J=1.2, 2 Hz, 1H]; 6.4 (dd, J=0.6, 2.1 Hz, 1H); 5.06 (s, 5.04, 2H); 5.04 (s, 2H); 4.97 (d, J=4.8 Hz, 4H); 4.87 (s, 2H); 3.03 (t, J=8.4 Hz, 2H); 2.83 (t, J=8.2 Hz, 2H) ppm.

Step 3. 2'-fluorophosphphloretin (2'-FPP)

Dibenzylphosphotribenzyl phloretin was dissolved in ethyl acetate. Palladium on carbon (200 mg of 10%) was added, and the solution was stirred under H$_2$ gas for 2 hours. The solution was filtered through Celite (Sigma-Aldrich). The Celite cake was washed twice with ethyl acetate, and the combined washes were concentrated under reduced pressure to yield 2'-PP (400 mg, 29% yield) after drying: melting point (mp), 171-172° C., $^1$H-NMR (d$_6$-DMSO) δ 13.0 (s, 1H); 10.7 (bs, 1H); 9.2 (bs, 1H); 7.03 (d, J=8.6 Hz, 2H); 6.64 (d, J=8.4 Hz, 2H); 6.63 (dd, J=1.2, 2.1 Hz, 1H); 2.77 (d, J=7.6 Hz, 2H) ppm.
$^{31}$P-NMR in D$_2$O yielded a single peak at 4 ppm composed of 98% of the phosphorus signal. $^{31}$P-NMR in DMSO yielded a single peak at 4.3 pulses/min. H-decoupled $^{13}$C-NMR experiments gave 12 unique carbon species that could be assigned to the inhibitor.

Electrospray mass spectrometry gave a mass/ion charge of 355 (mass+proton) consistent with the calculated molecular mass of 2'-PP of 354.

2'-PP was passed through an ion exchange column equilibrated with 100 mM tetramethylammonium bicarbonate, concentrated under vacuum and added to 10 mM DNFB. The reaction was stirred at 23° C. for 4 hours, and the reactants were washed through a silica gel column eluting with chloroform:methanol (70%:30%). Fractions were dried and precipitated with 0.1 M NaOH. The precipitate was collected, buffer exchanged through a Sephadex G-10 column and concentrated under vacuum.

Example 2

Synthesis of 2'-fluorophosphophloretin (2'-FPP) Using Hydrofluoric Acid

An alternative synthesis of 2'-FPP was performed substituting hydrofluoric acid for DNFB.

Starting with 20 mg of 2'-PP dissolved in 1 ml. DMF, 0.1 ml of 0.1 M HF was added and the solution allowed to sit at 23° C. for 2 hours. The reaction mixture was cooled, and neutralized to pH 8 with 12 N NaOH. The precipitated products were passed through a Sephadex G-10 column equilibrated with 100 mM TMAHCO$_3$ and lyophilized.

2'-FPP purity was examined by thin layer chromatography on silica gel using chloroform:methanol (7:3), or chloroform: 3-propanol (8:2). Analysis of 2'-FPP following TLC was performed by comparison by phloretin and 2'-PP. TLC plates were examined for phosphate by Fiske-SubbaRow reaction and for fluoride with Zirconium-alizarin lake HCl. A positive reaction with alizarin lake required heating the TLC strip for 1 hour at 60° C. $^1$H-NMR (d$_6$-DMSO) δ 10.7 (s, 1H); 9.3, (s, 1H); 7.17 (t, 2H J=8.6 Hz), 6.8 (t, 2H); 6.6 (d, 2H, J=8.4 Hz); 3.2 (t, 2H, J=2 Hz); 2.9 (t, 2H, J=2.1 Hz); 1.9 (weak singlet) ppm.

Example A

Effects of 2'-FPP on Na-Dependent [$^{32}$P] Phosphate Uptake

The effect of 2'-FPP on Na-dependent [$^{32}$P] phosphate uptake into intestinal brush border membrane (apical) vesicles was examined using rapid mixing rapid filtration experiments and liquid scintillation counting of filter retained counts in the presence of 100 mM Na or 100 mM K cis (inward) directed gradients. 2'-PP and 2'-FPP both inhibited Na-dependent phosphate uptake into intestinal brush border membrane vesicles. 2'-FPP was 12× more potent than 2'-PP in inhibiting Na-dependent phosphate uptake. The apparent IC$_{50}$ for 2'-PP was 46 nM±8 nM (n=4) similar to previous results (Peerce et al., *Biochem. Biophys. Res. Comm.* 301:8-12, 2003; Peerce and Clarke, *AM. J. Physiol.* 283:G848-G855, 2002). The IC$_{50}$ for 2'-FPP was 3.6 nM±0.6 nM (n=4).

Example B

The Effect of Phosphophloretins on P-Nitrophosphate Hydrolysis by Rat Alkaline Phosphatase and Intestinal BBMV Phosphatases The results shown in Example A used a 3-second exposure of vesicles and substrates and a 5 minute exposure of vesicles to 2'-FPP. Prior exposure and degradation of 2'-PP in contrast to 2'-FPP could be contributing to the increased potency of 2'-FPP as compared to 2'-PP. To examine this possibility the effect of phosphophloretins on p-nitrophosphate hydrolysis by rat alkaline phosphatase and intestinal BBMV phosphatases was examined.

2'-PP is a better inhibitor of alkaline phosphatase activity and intestinal BBMV phosphatase activity than 2'-FPP. 2 mM 2'-PP resulted in approximately 50% inhibition of intestinal BBMV phosphatase activity as compared to less than 10% inhibition by 2'-FPP. Consistent with the interpretation that the potency of 2'-PP as an inhibitor of Na-dependent phosphate uptake was limited by phosphatase mediated hydrolysis of 2'-PP, addition of alkaline phosphatase inhibitors (ascorbic acid+cysteine) decreased the IC$_{50}$ for 2'-PP inhibition of Na-dependent phosphate uptake 34% (from 38 nM to 26 nM). These results indicate that compared to 2'-PP, 2 factors are responsible for the increased potency of 2'-FPP as an inhibitor or Na-dependent phosphate uptake into intestinal brush border membrane vesicles: 1) increased resistance of 2'-FPP to phosphatase catalyzed degradation of phosphate ester, and 2) increased affinity of fluorophosphates for the intestinal Na-phosphate cotransporter phosphate site compared to phosphate.

Example C

Duration of Effect of a Single Exposure of Rat Intestine to 2'-FPP and 2'-PP

To examine the duration of the effect of a single dose of 2'-FPP on phosphate uptake, intestinal strips were cut (approximately 5-cm squares) and incubated in 12 well cell culture plates in the presence of 2'FPP or 2'-PP for 1 hour, followed by exposure to fresh DMEM (Debecco's Modified Eagles Medium), [$^{32}$P] phosphate and varying concentrations of 2'-PP or 2'-FPP.

A single exposure to 2'-FPP resulted in greater than 60% inhibition of phosphate uptake and that the inhibition was stable for 6 hours post-drug exposure. In contrast exposure to 2'-PP resulted in 40% inhibition of phosphate uptake which decreased to less than 35% inhibition 6 hours post-drug exposure. Glucose uptake was unaffected by exposure to either 2'-PP or 2'-FPP consistent with previous reports that phopshophloretins are specific for Na-phosphate cotransport, and that intestinal strips were viable during the course of the experiment.

These experiments were expanded to examine the effect of 2'-FPP concentration on phosphate uptake.

Rat duodenum/jejunum intestinal strips 1 cm square were incubated in DMEM at 37° C. and 5% $CO_2$ for one hour. After the incubation period, the DMEM was replaced containing 2'-FPP and the strips were incubated for an additional hour. After the 1 hour exposure to 2'-FPP, DMEM was replaced with fresh media +5 μCi of [$^{32}$P] phosphate. The strips were exposed to tracer phosphate for 1 hour, precipitated with 10% TCA and centrifuged at 5000 g for 30 minutes. An aliquot of the supernatant was taken for scintillation counting.

Na-dependent phosphate uptake in the intestine is composed of both Na-dependent and Na independent components. Na-dependent uptake into duodenum and jejunum is approximately 70% Na-dependent and 30% Na-independent phosphate uptake. The results are consistent with 2'-FPP inhibiting the Na-dependent component which is driven by the intestinal brush border membrane Na/phosphate cotransporter, NaPi 2b. Maximum inhibition was 67%±5% (n=4) of total phosphate absorption. The apparent $IC_{50}$ for 2'-FPP was 160 nM±20 nM (n=4). This compares with a maximum inhibition under identical conditions of 43±6% (n=3) for 2'-PP, and an $IC_{50}$ of 15 μM±3 μM (n=3).

Example D

The effect of 2'-FPP on serum phosphate and serum calcium in 4-5 month old adult rats with normal renal function was examined. Rats were gavaged daily with 3 ml of 0.5 μM 2'-FPP in phosphate buffered saline pH 7. Approximately 30 minutes later rats were exposed to food for 3 hours. After the feeding period, food was removed. Rats had ad libitum exposure to water. On the 3$^{rd}$ day of the experiment, blood was drawn from the tail vein, prior to gavage. Animals were then gavaged as before, and exposed to food. This process was repeated on days 5, 8, 11, and 14. On day 14 animal were sacrificed and the experiment terminated. Serum phosphorus, calcium, and BUN were determine using clinical kits.

Serum phosphorus decreased 52%±6% (n=8) in adult rats with normal renal function within the first week of treatment with 2'-FPP and remain stable at 3 mg/dL for the remainder of the 2-week experiment. Serum $Ca^{2+}$ was unaffected by 2'-FPP decreasing less than 2.5% during the 2-week exposure to 2'-FPP. BUN was 10 mg/dl at the start of the experiment and did not change over the course of the experiment. Previous experiments under identical conditions performed with 25 μM 2'-PP resulted in a 30%±4% decrease in serum phosphorus with no change in serum $Ca^{2+}$.

What is claimed is:
1. A compound of Formula I:

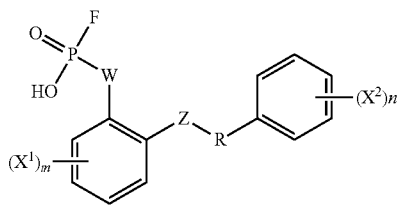

or a pharmaceutically acceptable salt thereof, wherein:
R is $C_{2-4}$ alkyl;
W is selected from $NR^A$, O, and S;
Z is selected from a single bond, —C(O)—, $NR^A$, O, and S;

$X^1$ and $X^2$ are each independently selected from —OH, —$NHR^A$, and —C(O)OH;
$R^A$ is H or $C_{1-3}$ alkyl;
m is 1, 2, 3, or 4; and
n is 1, 2, 3, or 4.

2. The compound of claim 1, or a pharmaceutically acceptable salt thereof, wherein R is —$CH_2$—$CH_2$— or —$CH_2$—$CH_2$—$CH_2$—.

3. The compound of claim 1, or a pharmaceutically acceptable salt thereof, wherein W is selected from $NR^A$ and O.

4. The compound of claim 1, or a pharmaceutically acceptable salt thereof, wherein W is O.

5. The compound of claim 1, or a pharmaceutically acceptable salt thereof, wherein Z is selected from a single bond and —C(O)—.

6. The compound of claim 1, or a pharmaceutically acceptable salt thereof, wherein Z is —C(O)—.

7. The compound of claim 1, or a pharmaceutically acceptable salt thereof, wherein $X^1$ and $X^2$ are independently selected from OH and $NH_2$.

8. The compound of claim 1, or a pharmaceutically acceptable salt thereof, wherein $X^1$ and $X^2$ are both OH.

9. The compound of claim 1, or a pharmaceutically acceptable salt thereof, wherein n is 1 or 2.

10. The compound of claim 1, or a pharmaceutically acceptable salt thereof, wherein m is 1 or 2.

11. The compound of claim 1, or a pharmaceutically acceptable salt thereof, wherein m is 2 and n is 1.

12. The compound of claim 1, or a pharmaceutically acceptable salt thereof, wherein R is —$CH_2$—$CH_2$— and Z is —C(O)—.

13. The compound of claim 1, or a pharmaceutically acceptable salt thereof, wherein W is O, and $X^1$ and $X^2$ are both OH.

14. A compound of claim 1, or a pharmaceutically acceptable salt thereof, wherein the compound is:

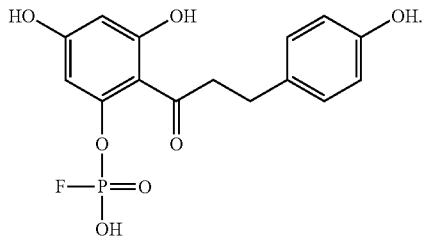 [SMILES: O=C(CCc1ccc(O)cc1)c1c(O)cc(O)cc1OP(=O)(O)F]

15. A compound of claim 1, wherein the compound is:

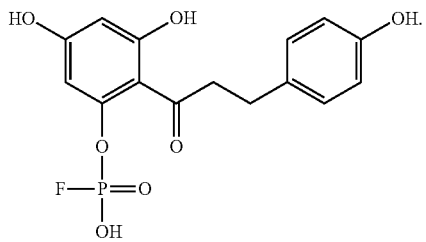 [SMILES: O=C(CCc1ccc(O)cc1)c1c(O)cc(O)cc1OP(=O)(O)F]

16. A composition comprising a compound of claim 1, or a pharmaceutically acceptable salt thereof, and at least one pharmaceutically acceptable carrier.

17. A method for treating a disease caused by or associated with elevated blood phosphate levels in a patient in need thereof, the method comprising administering to said patient a therapeutically effective amount of a compound or composition of claim 1.

18. The method of claim 17 wherein said disease is chronic renal failure.

19. The method of claim 17, wherein the compound is:

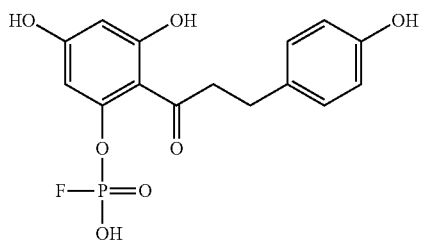 [SMILES: O=C(CCc1ccc(O)cc1)c1c(O)cc(O)cc1OP(=O)(O)F]

or a pharmaceutically acceptable salt thereof.

20. A process for preparing a compound of Formula I:

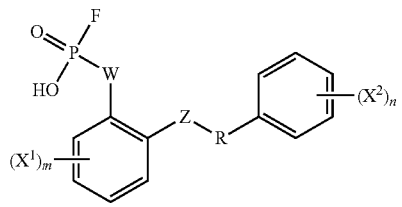

or a pharmaceutically acceptable salt thereof, wherein R is $C_{2-4}$ alkyl;
W is selected from $NR^4$, O, and S; Z is selected from a single bond, —C(O)—, $NR^4$, O, and S; $X^1$ and $X^2$ are each independently selected from —OH, —$NHR^4$, and —C(O)OH;
$R^4$ is H or $C_{1-3}$ alkyl; m is 1, 2, 3, or 4; and n is 1, 2, 3, or 4; the process comprising:
a) removing $Pr^1$ in the presence of $Pr^2$ from a compound of Formula I-1:

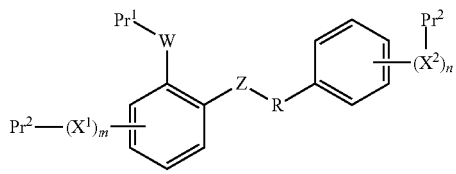

wherein $Pr^1$ and $Pr^2$ are protecting groups; to prepare a compound of Formula 1-2:

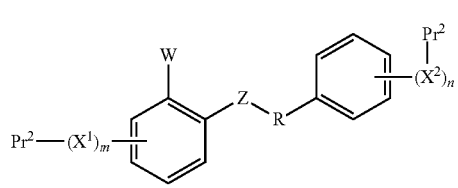

b) reacting a compound of Formula 1-2 with a phosphorylating agent to prepare a compound of Formula 1-3:

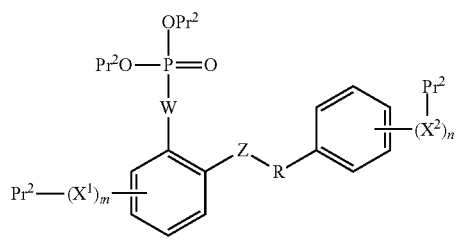

c) removing $Pr^2$ from a compound of Formula 1-3 with a reducing agent to prepare a compound of Formula 1-4:

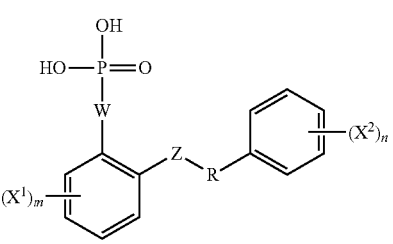

d) reacting a compound of Formula 1-4 with a fluorinating agent to prepare said compound of Formula I.

* * * * *